United States Patent [19]

Martin

[11] Patent Number: 4,911,692

[45] Date of Patent: Mar. 27, 1990

[54] STERILE STORAGE AND MIXING DISPENSER

[76] Inventor: James H. Martin, 8322 County Line Rd., Burr Ridge, Ill. 60521

[21] Appl. No.: 215,336

[22] Filed: Jul. 5, 1988

[51] Int. Cl.[4] .................................... A61M 5/00

[52] U.S. Cl. .................................... 604/89; 604/416

[58] Field of Search .................... 604/56, 82, 87–92, 604/410, 416

[56] References Cited

U.S. PATENT DOCUMENTS

| | | | |
|---|---|---|---|
| 2,609,818 | 9/1952 | Parrine | 604/200 X |
| 2,744,527 | 5/1956 | Barrett et al. | 604/89 |
| 4,410,321 | 10/1983 | Pearson et al. | 604/82 X |
| 4,583,971 | 4/1986 | Bocquet et al. | 604/82 |
| 4,692,151 | 9/1987 | Blackman | 604/132 |
| 4,735,608 | 4/1988 | Sardam | 604/89 |

*Primary Examiner*—Dalton L. Truluck
*Attorney, Agent, or Firm*—Edmond T. Patnaude

[57] ABSTRACT

An intravenous fluid dispenser includes two reservoirs, and containing a predetermined quantity of a liquid under pressure and the other containing a predetermined quantity of a material to be mixed with the liquid; a conduit extends between the two reservoirs and a manually operable valve in the conduit is used to controllably connect the reservoirs together to cause the liquid to flow at a high velocity into the second reservoir. An outlet conduit extends from the bottom of the second reservoir for conveying the mixed solution to a patient.

12 Claims, 1 Drawing Sheet

STERILE STORAGE AND MIXING DISPENSER

The present invention relates in general to a storage and dispensing container for dispensing a fluid mixture, and it relates more particularly to a dispenser in which a solvent and a solute are stored in sterile, mutually isolated chambers and are adapted to be mixed together under conditions of absolute sterility a short time before use of the mixture.

BACKGROUND OF THE INVENTION

Some solutions have a relatively short useful life after a solute is mixed with a solvent. Once such solution is a thrombolytic agent which is supplied intravenously to a patient to dissolve blood clots. The solution must be used within a few hours after the thrombolytic agent, in powder form, is dissolved in a liquid carrier such as water. At the present time, when the solution is to be administered, a nurse or other person adds a prescribed quantity of the liquid solvent into a vessel containing a prescribed quantity of the thrombolytic powder and shakes or otherwise mixes the mixture to accelerate the dissolution of the powder in the solvent. The solution must be administered shortly thereafter.

It would be desirable to provide a more sterile and foolproof system for shipping, storing and subsequently mixing a solvent and a solute to insure a precise mixture of premeasured quantities of the solvent and the solute under completely sterile conditions.

SUMMARY OF THE INVENTION

Briefly, there is provided in accordance with the present invention a liquid dispenser including an hermetically sealed reservoir containing a premeasured quantity of a liquid solvent under pressure, a hermetically sealed, flexible and pliable bag containing a premeasured quantity of a solute and a manually operable valve for connecting said reservoir to said bag to permit said solvent to flow under pressure into said bag for rapid dissolving of the solute in a totally closed and sterile system. An outlet tube from the bag is adapted to be connected to a cannula for insertion into the body of a patient, and the flexibility of the bag permits the use of gravity for feeding the solution to the patient under completely sterile conditions.

In accordance with another important aspect of the invention, a detent is incorporated into the valve to deter reclosure of the valve once it has been opened thereby to prevent an improper mixture of a reduced quantity of the solvent with the solute.

GENERAL DESCRIPTION OF THE DRAWING

Further objects and advantages and a better understanding of the present invention will be had by reference to the following detailed description taken in connection with the accompanying drawings wherein.

DETAILED DESCRIPTION OF A PREFERRED EMBODIMENT

Figure 1:
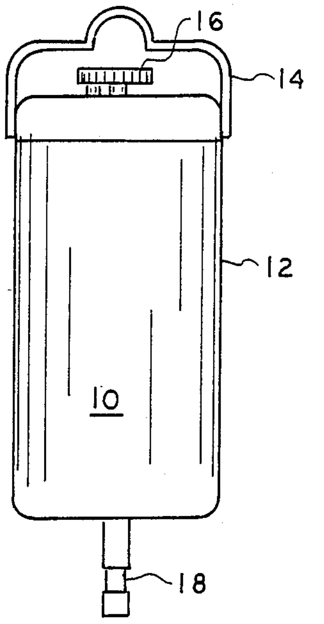
FIG. 1 is an elevational view of a storage, mixing and dispensing container embodying the present invention.

In FIG. 1 there is shown a mixing and dispensing device 10 which comprises a generally cylindrical housing 12 having a generally U-shaped bail 14 attached near the top and extending across the top of the housing for hanging the device 10 on a hook or the like during intravenous feeding of a patient with a solution contained in the device 10. A rotatable knob 16 extends from the top of the housing 12 and is adapted to be manually rotated to open a valve (not shown in FIG. 1) to mix together a solvent and a solute which are stored in separate sterile compartments within the housing 12. After the solvent and solute have bee mixed as is evident from the position of the knob 16 as explained in greater detail hereinafter, the mixed solution may be fed through a flexible supply tube 18 which extends from the bottom of the housing 12 via a suitable flexible tube to a cannula which is adapted to be inserted into the patient. Preferably, the container 12 is transparent or is provided with a window to permit the attendant to visually observe that the mixture has taken place.

Figure 2:
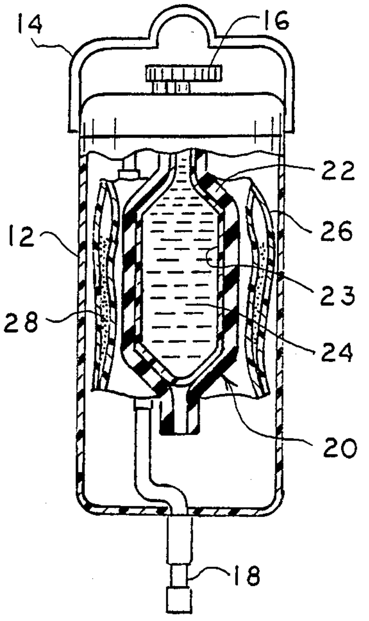
FIG. 2 is an elevational view of the container of FIG. 1 with portions broken away to show the internal operating parts thereof prior to mixing a stored solvent with a stored solute.
Figure 3:
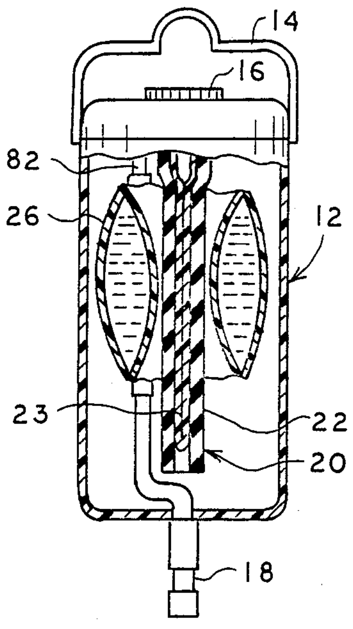
FIG. 3 is a fragmentary elevational view similar to that of FIG. 2 but showing the container after the solvent and the solute have been mixed.

Referring to FIG. 2, it will be seen that located within housing 12 is an elastomeric reservoir 20 which includes a rubber sleeve 22 enclosing an expandable and contractible plastic reservoir 23 which contains a solvent 24 under pressure by virtue of the fact that the sleeve 22 is expanded from its normal unstressed state as shown in FIG. 3. The reservoir 20 is preferably of the type described in U.S. Pat. No. 4,387,833. The plastic container 23 is impervious to gas wherefor the solvent 24 contained therein is hermetically sealed from the ambient and is thus maintained in a sterile condition.

Wrapped around the reservoir 20 is a flexible and pliable plastic bag 26 formed of a gas impervious, transparent material, and a solute 28, which is shown in powder form, is contained within the bag 26. It will be understood that the solute 28 may be another liquid where desired. As shown in FIG. 2 the bag 26 itself is in a substantially flat or compressed condition.

Figure 4:
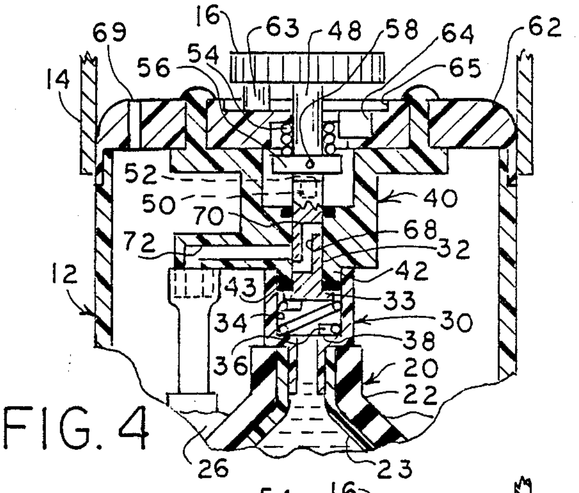
FIG. 4 is a vertically sectioned view of the upper part of the container of FIG. 1 particularly showing the mixing valve which connects the solvent reservoir to the solute bag, the valve being shown in the closed condition.
Figure 5:
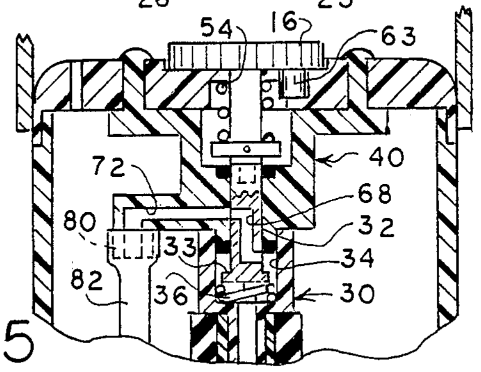
FIG. 5 is a view similar to that of FIG. 4 but sowing the valve in the open condition.

When the valve control knob 16 is rotated through 180 degrees from the closed position shown in FIG. 2 to the open position shown in FIG. 3, the knob 16 is automatically withdrawn a substantial distance into a recess in the top wall of the container 12 as shown in FIG. 3, and the control valve, which is shown in FIGS. 4 and 5 snaps into the fully open position and abruptly connects the chamber in the container 23 to the chamber within the container 26. Inasmuch as the chamber within the container 23 is under pressure, when the valve is opened the solvent 24 contained in the container 23 is forced under pressure at high velocity into the bag 28 where it rapidly mixes with the solute 26 which is rapidly dissolved into the solvent so that the bag 26 contains a substantially homogenous solution of the solvent and the solute a short time after the valve is opened. As may be seen in FIG. 3, the flexible tube 18 is connected to the bottom of the bag 26, and when the distal end of the tube 18 is connected to an intravenous tube (not shown) and the container 12 is in the upright position as shown in FIG. 3 the solution in the flexible bag 26 will flow under the force of gravity into the patient. As explained more fully in connection with FIGS. 4 and 5, the chamber within the housing 12 is connected to the atmosphere whereby the bag 26 collapses as the mixed solution flows to the patient. The entire system is, therefore, closed and it is totally and hermetically sealed from the atmosphere so that the storage of the solute and solvent, the mixing of the two together and the subsequent feeding of the mixed solution to the patient may take place under completely sterile conditions. The system is thus well suited for use in an ambulance as well as in a hospital.

Referring now to FIG. 4 for a more detailed description of the control valve which is operated by the knob 16, there is shown a tubular connector 30 having a reduced diameter portion at the bottom which extends into the neck at the top of the container 23 and is sealably attached thereto by a suitable adhesive. The upper and large diameter portion of the connector 30 receives the lower end of an axially moveable and rotatable valve stem 32 which includes an annular external flange 33 at its lower end. The lower end of the valve stem is loosely slidable in the bore 34 of the connector 30. A coil spring 36 is also loosely fitted within the bore 34 and is compressed between an upwardly facing shoulder 38 on the connector 30 and the lower end of the valve stem 32.

A generally tubular housing member 40 includes a depending tubular portion of reduced diameter which is tightly fitted into the upper end of the bore 34 and a sealing gasket 43 is positioned between the lower end of the housing 40 and the flange 33 on the valve stem 32.

Depending from the knob 16 is an integral shaft 48 having at the bottom a connector 50 which is square in cross section and which is adapted to be received in a complementary recess 52 in the top of the valve stem 32 whereby rotation of the knob 16 causes corresponding rotation of the valve stem 32. A coil spring 54 is compressed between a bottom surface of the top member 62 of the container 12 and a washer 56 which is fixed to the shaft 48 by a transverse pin 58. The coil spring 54 biases the knob 16 in a downward direction. A stud 63 which is integral with the knob 16 and depends therefrom prevents downward movement of the knob 16 and the valve stem 32 while the knob 16 is not at the open position as shown in FIG. 2. When, however, the knob is rotated through 180 degrees to the open position the stud 63 is aligned with a blind hole 64 in the top of the member 62 whereby the spring 54 pulls the lower portion of the knob 16 into a shallow circular recess 65 in the top member 62.

A passageway 68 is provided in the valve stem 32, and when the knob 16 is in the closed position the passageway is closed at both the top and bottom by the wall of the bore 70 through the housing 40. When, however, the valve stem is moved to its downward position and rotated through 180 degrees to the open position as illustrated in FIG. 5, it will be seen that the passageway 68 is connected between the bore 34 in the connector 30 and a conduit 72 in the housing member 40. The conduit 72 extends through a tubular portion of the housing over which is press fitted the upper end 80 of a resilient sleeve 82 which is connected to the top of the bag 26. Therefore, when the valve is open, the fluid in the container 23 flows past the spring 36 and around the edges of the flange 33 into the passageway 68 in the valve stem 32 and thus flows at a high velocity into the bag 26 where it rapidly mixes with the solute contained therein. The spring 54 holds the knob in the down position and the stud 63 prevents rotation thereof. Accordingly, once the knob is rotated to the valve opening position, the spring 54 causes the abrupt opening of the valve and prevents its being reclosed. As a result, the predetermined quantity of the solvent 24 contained in the reservoir 20 is mixed with the predetermined quantity of the solute 28 whereby the chance of error in the quantity of either of these materials in the final solution is minimized.

The dispenser 10 enables the facile and rapid mixing of the solvent and solute under adverse conditions, as for example, in an ambulance where the transfer of the solvent or solute from one container to another is at best difficult. Moreover, both the solvent and the solute are stored under completely sterile conditions and the mixing of the two also takes place in a closed system under completely sterile conditions so that any chance of contamination of the products during the mixing operation and subsequent storage is completely eliminated, and possible contamination during feeding of the mixed solution to the patient is also minimized since no handling of the solution is required.

While the present invention has been described in connection with a particular embodiment thereof, it will be understood by those in the art that many changes may be made without departing from the true spirit and scope of the present invention. Therefore, it is intended by the appended claims to cover all such changes and modifications which come within the true spirit and scope of this invention.

What is claimed:

1. An intravenous fluid dispenser, comprising in combination:
   - a reservoir having a chamber therein containing a predetermined quantity of a liquid under pressure,
   - a flexible container having a chamber therein containing a predetermined quantity of a material to be mixed with said liquid,
   - a conduit extending between said chambers,
   - a manually operable valve means connected in said conduit for controllably connecting said chambers together to cause said liquid to flow into said chamber in said flexible container, and
   - an outlet conduit extending from said flexible container for conveying liquid from said flexible container to a patient.

2. A intravenous fluid dispenser according to claim 1, wherein said reservoir comprises
   - a collapsible container, and
   - an elastomeric sleeve enclosing said collapsible container.

3. An intravenous fluid dispenser according to claim 2 wherein said valve means comprises
   - a valve movable between a closed position and an open position, and
   - means inhibiting the closing of said valve after it has been moved from said closed position to said open position.

4. An intravenous fluid dispenser according to claim 1, comprising
   - an outer housing,
   - said reservoir and said flexible container being disposed in said housing,
   - means connected to said housing near the top thereof for hanging said housing from a support, and
   - said outlet conduit extending from the bottom of said housing.

5. An intravenous fluid dispenser according to claim 1 wherein said flexible container comprises
an hermetically sealed, impervious plastic bag, and
said chamber in said reservoir is sealed from the ambient.

6. An intravenous fluid dispenser according to claim 5, wherein said valve means comprises valve actuator means movable from a closed position to an open position, and
spring means for opening said valve means when said valve actuator means is in said open position.

7. An intravenous fluid dispenser, comprising in combination:
a reservoir including a collapsible container enclosing a chamber containing a predetermined quantity of a liquid solvent and an elastomeric sleeve enclosing said container and maintaining said chamber under pressure,
a flexible container having a chamber therein containing a predetermined quantity of a material to be mixed with said solvent,
said flexible container at least partially surrounding said elastomeric sleeve,
an outer housing formed of a rigid material enclosing said reservoir and said flexible container,
a conduit extending between said collapsible container and said flexible container,
a valve disposed in said conduit,
manually operated means mounted to said housing for opening said valve to permit said liquid solvent to flow from said reservoir into said flexible container and to mix with said material, and
an outlet conduit extending from the bottom of said flexible container to an outlet at the bottom of said housing.

8. An intravenous fluid dispenser according to claim 7, wherein
said housing is vertically elongate, and
said manually operated means is located at the top of said housing, 9. An intravenous fluid dispenser according to claim 8, wherein
said manually operated means includes a rotatable actuator member extending from the top of said housing.

10. An intravenous fluid dispenser according to claim 9 wherein said rotatable actuator member is rotatable between a closed position and an open position, and said manually operated valve further includes
spring loaded detent means responsive to the movement of said actuator member to said open position for locking said actuator member in said open position.

11. An intravenous fluid dispenser according to claim 10, wherein said manually operated valve means comprises
a valve housing having first and second ports respectively connected to said flexible container and to the chamber in said collapsible container,
a valve stem rotatable in said housing between a first position and a second position, and
a passageway in said valve stem positioned to connect said first port to said second port when said valve stem is in said second position.

12. An intravenous fluid dispenser according to claim 11, wherein
said second position of said valve stem is rotatably and axially displaced from said first position.

* * * * *